TODO

United States Patent
Catanese, III et al.

(10) Patent No.: US 8,529,584 B2
(45) Date of Patent: Sep. 10, 2013

(54) MEDIAN LOBE BAND IMPLANT APPARATUS AND METHOD

(75) Inventors: Joseph Catanese, III, San Leandro, CA (US); Brian Y. Tachibana, Oakland, CA (US); Matthew McLean, San Francisco, CA (US); Daniel Merrick, Dublin, CA (US); Theodore C. Lamson, Pleasanton, CA (US); Ling-Kang Tong, Fremont, CA (US); James Niederjohn, San Jose, CA (US); Floria Cheng, San Francisco, CA (US); Ben Thompson, San Carlos, CA (US)

(73) Assignee: Neotract, Inc., Pleasanton, CA (US)

( * ) Notice: Subject to any disclaimer, the term of this patent is extended or adjusted under 35 U.S.C. 154(b) by 288 days.

(21) Appl. No.: 12/979,078

(22) Filed: Dec. 27, 2010

(65) Prior Publication Data

US 2011/0160748 A1 Jun. 30, 2011

(51) Int. Cl.
*A61B 17/10* (2006.01)
(52) U.S. Cl.
USPC .......................... 606/139; 606/144; 606/145
(58) Field of Classification Search
USPC ................ 606/139, 140, 144–146, 148–151, 606/153, 157, 232
See application file for complete search history.

(56) References Cited

U.S. PATENT DOCUMENTS

| 659,422 A | 10/1900 | Shidler |
|---|---|---|
| 780,392 A | 1/1905 | Wanamaker et al. |
| 789,467 A | 5/1905 | West |
| 2,579,192 A | 12/1951 | Kohl |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,664,345 A | 5/1972 | Dabbs et al. |
| 3,713,680 A | 1/1973 | Pagano |
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |

(Continued)

FOREIGN PATENT DOCUMENTS

| DE | 10159470 | 6/2003 |
|---|---|---|
| EP | 0246836 | 12/1991 |

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007.

(Continued)

*Primary Examiner* — Gregory Anderson
(74) *Attorney, Agent, or Firm* — Steptoe & Johnson LLP

(57) ABSTRACT

A system and associated method for manipulating tissues and anatomical or other structures in medical applications for the purpose of treating diseases or disorders or other purposes. In one aspect, the system includes a delivery device configured to deploy and implant devices for compressing, distracting and/or retracting the lobes of a prostate.

20 Claims, 17 Drawing Sheets

(56) References Cited

U.S. PATENT DOCUMENTS

| | | |
|---|---|---|
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,080,660 A | 1/1992 | Buelna |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,267,960 A | 12/1993 | Hayman et al. |
| 5,269,809 A | 12/1993 | Hayhurst et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | de la Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | de la Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyar et al. |
| 5,810,848 A | 9/1998 | Hayhurst |
| 5,814,072 A | 9/1998 | Bonutti |
| 5,830,179 A | 11/1998 | Mikus et al. |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck, III |
| 6,010,514 A | 1/2000 | Burney et al. |
| 6,011,525 A | 1/2000 | Piole |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,159,234 A | 12/2000 | Bonutti et al. |
| 6,200,329 B1 | 3/2001 | Fung et al. |
| 6,206,895 B1 | 3/2001 | Levinson |
| 6,228,096 B1 | 5/2001 | Marchand |
| 6,258,124 B1 | 7/2001 | Darois et al. |

| Patent No. | Date | Inventor(s) |
|---|---|---|
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,290,711 B1 | 9/2001 | Caspari et al. |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Tanner et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,011,688 B2 | 3/2006 | Gryska et al. |
| 7,015,253 B2 | 3/2006 | Escandon et al. |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,481,771 B2 | 1/2009 | Fonseca et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |
| 2001/0044639 A1 | 11/2001 | Levinson |
| 2002/0095154 A1 | 7/2002 | Atkinson et al. |
| 2002/0128684 A1 | 9/2002 | Foerster |
| 2002/0161382 A1 | 10/2002 | Neisz et al. |
| 2002/0193809 A1 | 12/2002 | Meade |
| 2003/0109769 A1 | 6/2003 | Lowery et al. |
| 2003/0191497 A1 | 10/2003 | Cope |
| 2003/0204195 A1 | 10/2003 | Keane et al. |
| 2003/0236535 A1 | 12/2003 | Onuki et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly |
| 2004/0243227 A1 | 12/2004 | Starksen et al. |
| 2004/0260345 A1 | 12/2004 | Foerster |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1 | 7/2005 | Okada et al. |
| 2005/0177181 A1 | 8/2005 | Kagan et al. |
| 2005/0203344 A1 | 9/2005 | Orban, III et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | Starksen et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0276871 A1 | 12/2006 | Lamson et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |

| | | | |
|---|---|---|---|
| 2008/0009888 A1 | 1/2008 | Ewers et al. | |
| 2008/0021445 A1 | 1/2008 | Elmouelhi et al. | |
| 2008/0033458 A1 | 2/2008 | McLean et al. | |
| 2008/0033488 A1 | 2/2008 | Catanese, III et al. | |
| 2008/0039894 A1 | 2/2008 | Catanese, III et al. | |
| 2008/0045978 A1 | 2/2008 | Kuhns et al. | |
| 2008/0058710 A1 | 3/2008 | Wilk | |
| 2008/0065120 A1 | 3/2008 | Zannis et al. | |
| 2008/0082113 A1 | 4/2008 | Bishop et al. | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0119874 A1 | 5/2008 | Merves | |
| 2008/0154378 A1 | 6/2008 | Pelo | |
| 2008/0195145 A1 | 8/2008 | Bonutti et al. | |
| 2008/0208220 A1 | 8/2008 | Shiono et al. | |
| 2010/0010631 A1 | 1/2010 | Otte et al. | |
| 2010/0114162 A1 | 5/2010 | Bojarski et al. | |
| 2010/0286106 A1 | 11/2010 | Gat et al. | |
| 2010/0286679 A1 | 11/2010 | Hoey et al. | |
| 2011/0166564 A1 | 7/2011 | Merrick et al. | |

FOREIGN PATENT DOCUMENTS

| | | |
|---|---|---|
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 0464480 | 1/2008 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO 0230335 | 4/2002 |
| WO | WO 03/039334 | 5/2003 |
| WO | WO03/077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008443917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006—[Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 2009; 16 (1): 19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39, 1990.

O. Reich, et al. "Benignes Prostatasyndrom (BPS)", Der Urologe A Issue vol. 45, No. 6, Jun. 2006, p. 769-782.

Daito Takashi, "Low-Invasive Treatment for BPH", Medico vol. 34, No. 10, p. 366-369, 2003.

Trapeznikov et al., "New Technologies in the Treatment of Benign Prostatic Hyperplasia", Urologia Nefrol (Mosk) Jul.-Aug. 1996, (4):41-47.

Koyanagi Tomohiko, et al., "Surgery View of 21st Century", Urological Surgery, vol. 84, No. 1, p. 47-53, 2001.

Borzhievski, et al., "Tactics of the Surgical Treatment of Patients With Prostatic Adenoma and Acute Urinary Retention", Urologia Nefrol (Mosk), Jan.-Feb. 1987, (1):39-43.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

P. Schauer et al., "New applications for endoscopy: the emerging field of endoluminal and transgastric bariatric surgery," Surgical Endoscopy, Accepted Jun. 7, 2006.

Yeung, Jeff, "Treating Urinary Stress Incontinence Without Incision With Endoscopic Suture Anchor and Approximating Device," Aleeva Medical, Inc., 2007.

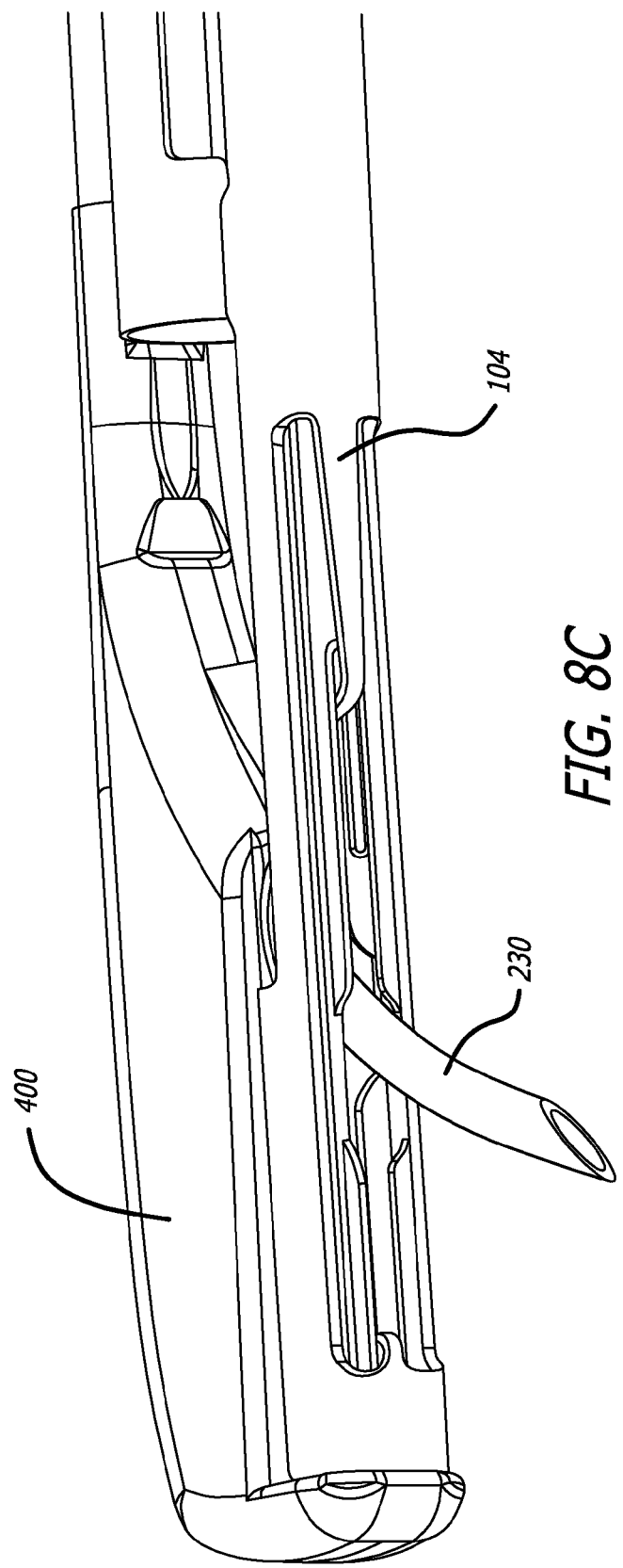

MEDIAN LOBE BAND IMPLANT APPARATUS AND METHOD

FIELD OF THE INVENTION

The present invention relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for cosmetic lifting and repositioning of tissues. For example, approaches have been proposed to displace and/or compress lobes of a prostate gland to receive pressure on and provide a less obstructed path through a urethra.

There remains, however, a need for the development of new devices and methods that can be used for various procedures where it is desired to lift, compress, support or reposition the lobes of a prostate. In particular, there is a need for alternative apparatus and treatment approaches for the purpose of manipulating median lobes of a prostate. Various structures ensuring an effective interventional procedure have been found to be needed.

The present disclosure addresses these and other needs.

SUMMARY

Briefly and in general terms, the present disclosure is directed towards an apparatus and method for deploying a band or other structure within a patient's body to accomplish retraction or displacement of an enlarged median lobe of a prostate to lessen obstruction or constriction of the urethra. A delivery device is provided to access the anatomy targeted for the interventional procedure, such as a median lobe. The delivery device facilitates the implantation of the band structure in a manner accomplishing compression, retraction or displacement of tissue.

The delivery apparatus of the present disclosure includes various subassemblies which are mobilized via an actuator or other manually accessible structure. The operation of the subassemblies is coordinated and synchronized to ensure accurate and precise implantation of a band implant.

In one particular aspect, the present disclosure is directed towards a delivery device which accomplishes the delivery of a band implant. The procedure can be viewed employing a scope inserted in the device. Also, the delivery device can be sized and shaped to be compatible inside a sheath in the range of 17 to 24 F, preferably a 19 F sheath or smaller.

The band implant can be configured to accomplish approximating, retracting, lifting, compressing, supporting or repositioning tissue within the body of a human or animal subject. Moreover, the apparatus configured to deploy the band implant as well as the band implant itself are configured to complement and cooperate with body anatomy. Further, the band implant can be coated or imbedded with therapeutic or diagnostic substances, in particular Botulinum toxin, or a silver ion coating or such substances can be introduced into or near an interventional site by the delivery device or other structure.

In various approaches, the band implant can be embodied in a tissue wire, a sling, a curved wire form, elastic loops, suture, or toggle bolt. The band implant structure provides surface contact and focuses the compressive forces upon a prostate lobe.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires approximately, retracting, lifting, repositioning, compression or support.

In a specific application, the disclosed apparatus are contemplated to be employed to, compress, retract or displace an enlarged median lobe of a prostate. In one aspect, a band implant housed within a delivery device is inserted into a prosthetic urethra transurethrally and the delivery device is employed to compress or displace the enlarged median lobe. The band implant is then used to maintain the median lobe in the compressed or displaced configuration. Further, the system can additionally include an ultrasound or other imaging probe.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIGS. 8A-F are various views of implant delivery devices;

DETAILED DESCRIPTION OF THE PREFERRED EMBODIMENTS

Turning now to the figures, which are provided by way of example and not limitation, the present disclosure is directed to a device configured to deliver a band implant within a patient's body for treatment purposes. The disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders such as the displacement, compression and/or retraction of the median lobe of a prostate.

With reference to FIGS. 1-4, various features of urological anatomy of a human subject are presented. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during ejaculation of sperm to expel semen and to provide a valve to keep urine out of the semen. A capsule C surrounds the prostate gland PG.

The urinary bladder UB holds urine. The vas deferentia VD define ducts through which semen is carried and the seminal vesicles SV secrete seminal fluid. The rectum R is the end segment of the large intestine and through which waste is dispelled. The urethra UT carries both urine and semen out of the body. Thus, the urethra is connected to the urinary bladder UB and provides a passageway to the vas deferentia VD and seminal vesicles SV.

Further, the trigone T (See FIG. 3) is a smooth triangular region of the bladder. It is sensitive to expansion and signals the brain when the urinary bladder UB is full. The verumontanum VM is a crest in the wall of the urethra UT where the seminal ducts enter. The prostatic urethra is the section of the urethra UT which extends through the prostate.

Figure 1:
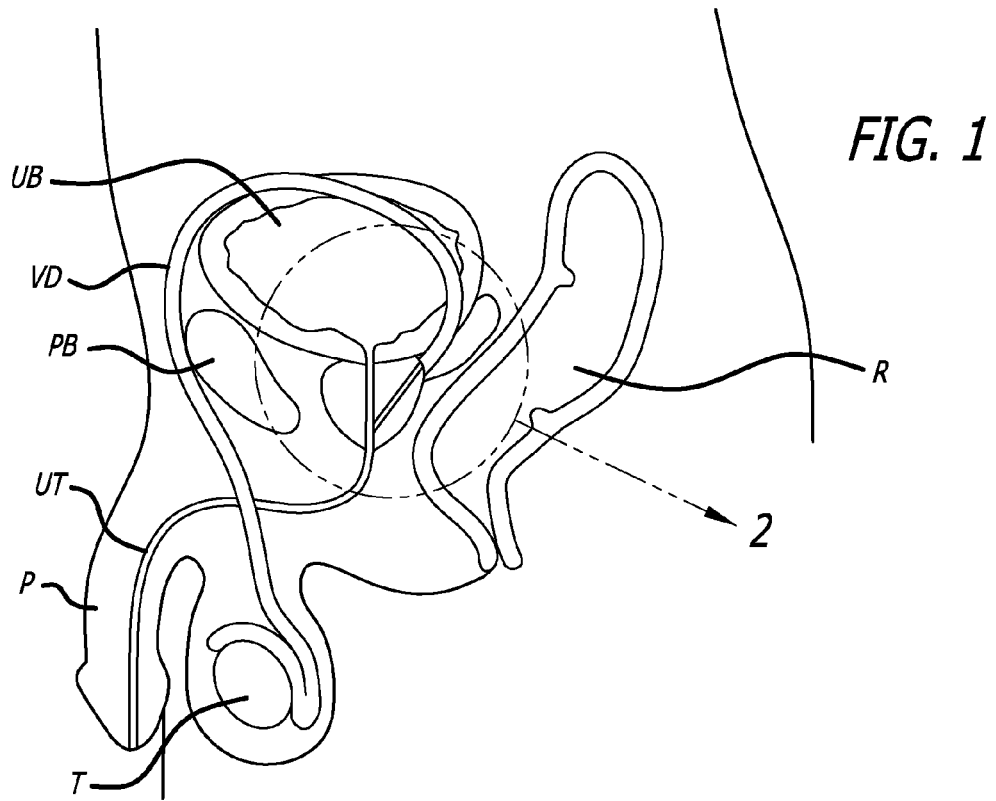
FIG. 1 is a cross-sectional view, depicting anatomy surrounding a prostate in a human subject.
Figure 2:
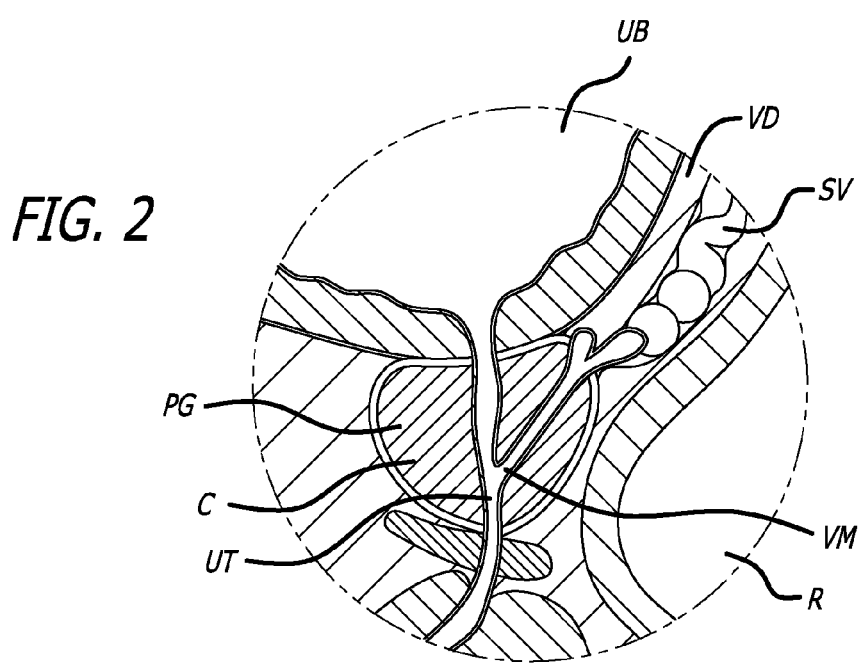
FIG. 2 is an enlarged cross-sectional view, depicting anatomy surrounding a prostate.
Figure 3:
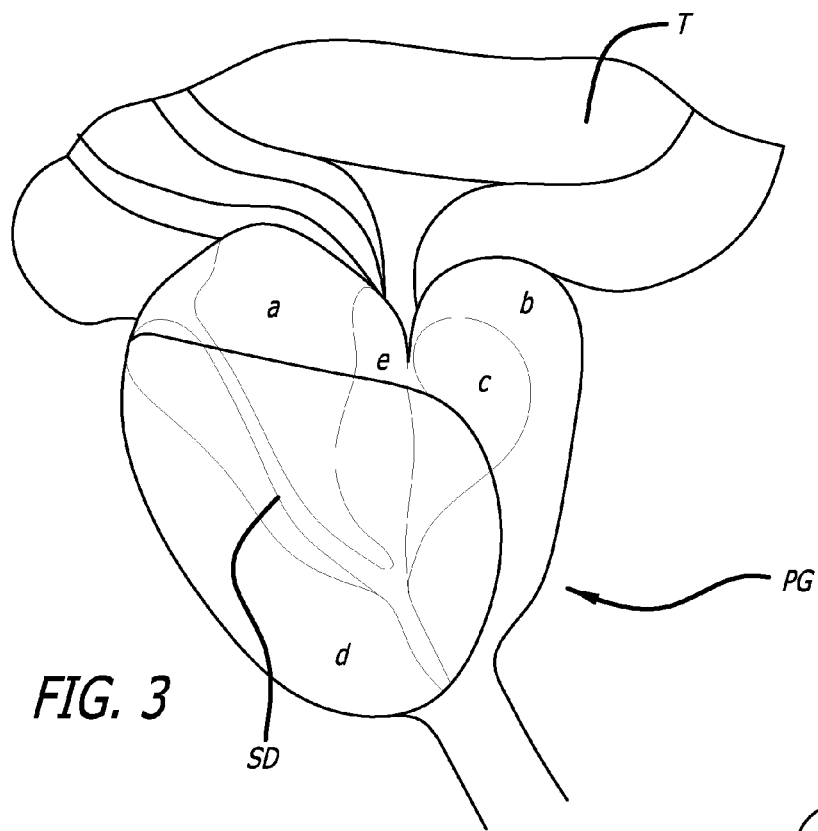
FIG. 3 is a schematic view, depicting prostatic anatomy zones.
Figure 4:
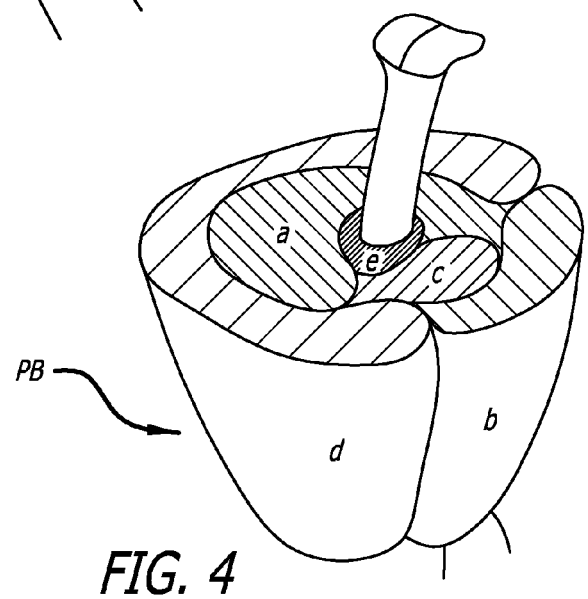
FIG. 4 is a schematic cross-sectional view, depicting further details of the anatomy zones shown in FIG. 3.

The prostate gland can be classified by zones or described by referring to its lobes (See FIG. 4). Whereas the zone classification is typically used in pathology, the lobe classification is more often used in anatomy. The central zone (a) of a prostate gland PG is about 25% of a normal prostate and this zone surrounds the ejaculating ducts. There is some prevalence of benign prostate hyperplasia in the transition zone. The fibromuscular zone (b) is usually devoid of glandular components and as its name suggests, is composed of only muscle and fibrous tissue. The transitional zone (c) generally overlays the proximal urethra and is the region of the gland that grows throughout life. Also, this lobe is often associated with the condition of benign prostatic enlargement. Finally, the peripheral zone (d) is the sub-capsular portion of the posterior aspect of the prostate gland that surrounds the distal urethra.

The lobe characterization is different from the zone characterization, but there is some overlap. The anterior lobe is devoid of glandular tissue and is completely formed of fibromuscular tissue. This lobe thus roughly corresponds to the anterior portion of the transitional zone (c). The posterior lobe roughly corresponds to the peripheral zone (d) and can be palpated through the rectum during a digital rectal exam. The posterior lobe is the site of 70-80% of prostatic cancers. The lateral lobe is the main mass of the prostate and is separated by the urethra. It has been described as spanning all zones. Lastly, the median lobe roughly corresponds to part of the central zone. It varies greatly in size and in some cases is devoid of glandular tissue.

A large or enlarged median lobe can act as a ball valve, blocking the bladder neck. Various approaches are contemplated to address such a condition. Thus, it is contemplated that the median lobe can be compressed, displaced and/or retracted to eliminate or decrease the blocking of the bladder neck.

Figure 5:
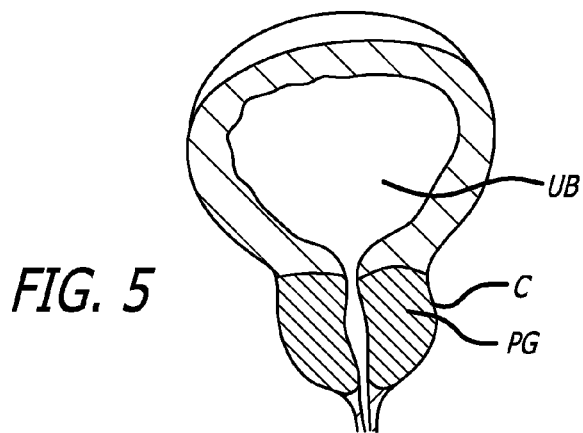
FIG. 5 is a cross-sectional view, depicting a normal prostate.
Figure 6:
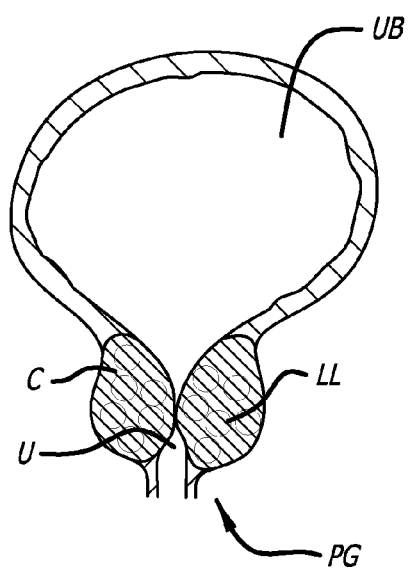
FIG. 6 is a cross-sectional view, depicting a prostate with enlarged lateral lobes.
Figure 7:
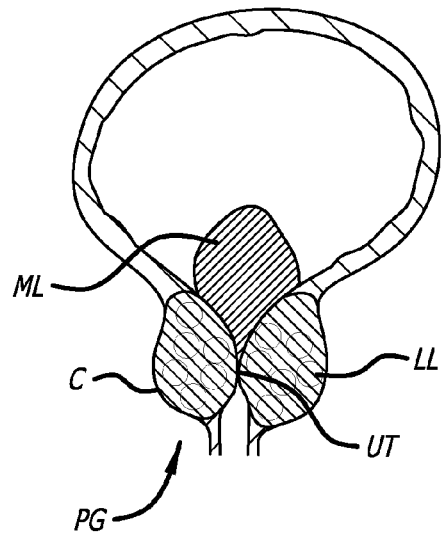
FIG. 7 is a cross-sectional view, depicting a prostate with enlarged lateral lobes and an enlarged median lobe.

Turning now to FIGS. 5-7, there are shown various prostate glands in cross-section. FIG. 5 depicts the urinary bladder UB and prostate gland PG of a healthy subject. FIG. 6 illustrates an individual with a prostate having enlarged lateral lobes LL and FIG. 7 depicts a subject suffering from both enlarged lateral lobes LL and an enlarged median lobe ML. It is to be appreciated that such enlarged anatomy impinges on the urethra UT and affects normal functioning. The following devices and approaches are intended to be employed to free up a path through the prostatic urethra.

Figure 8A:
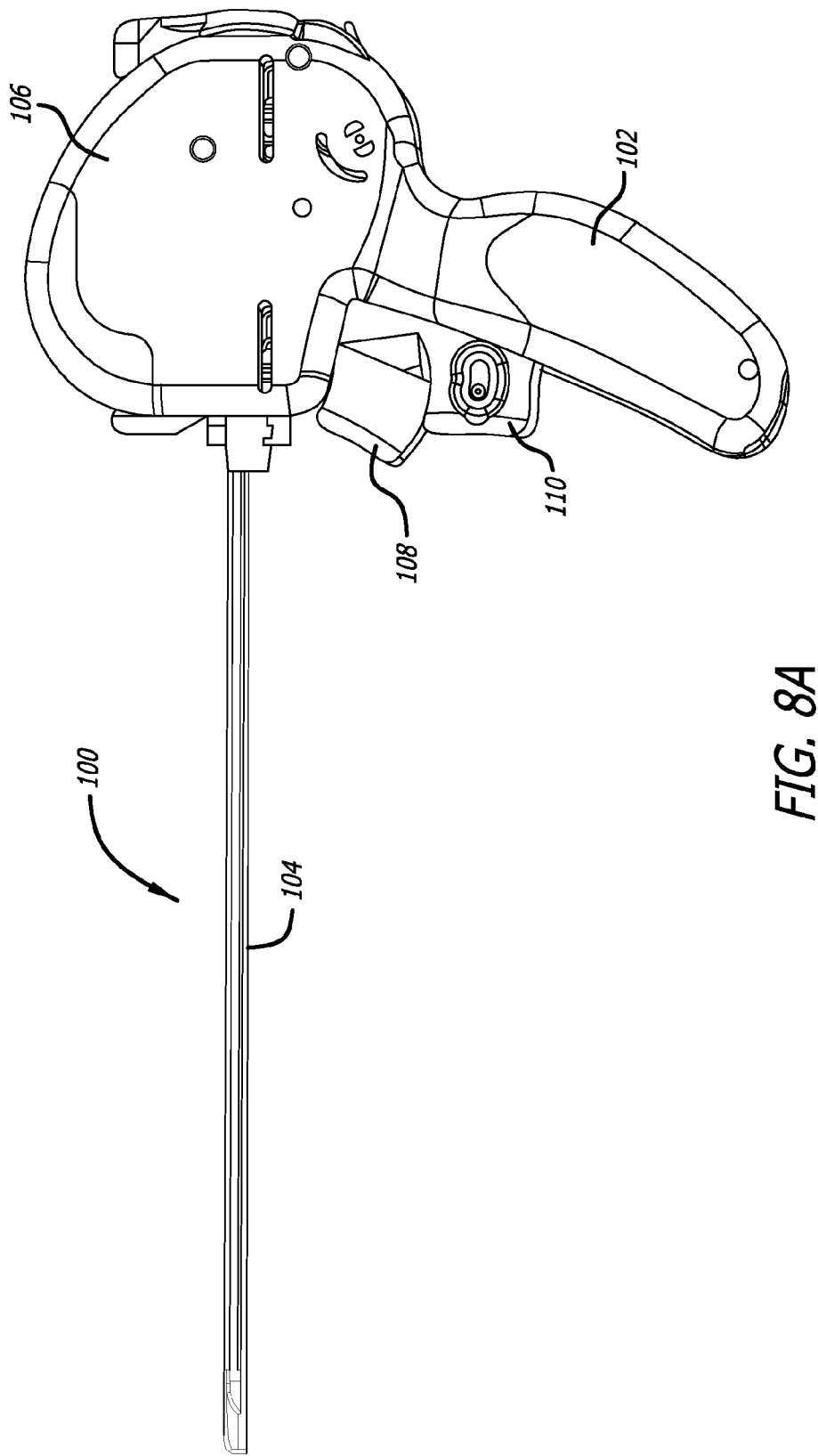
Figure 8B:
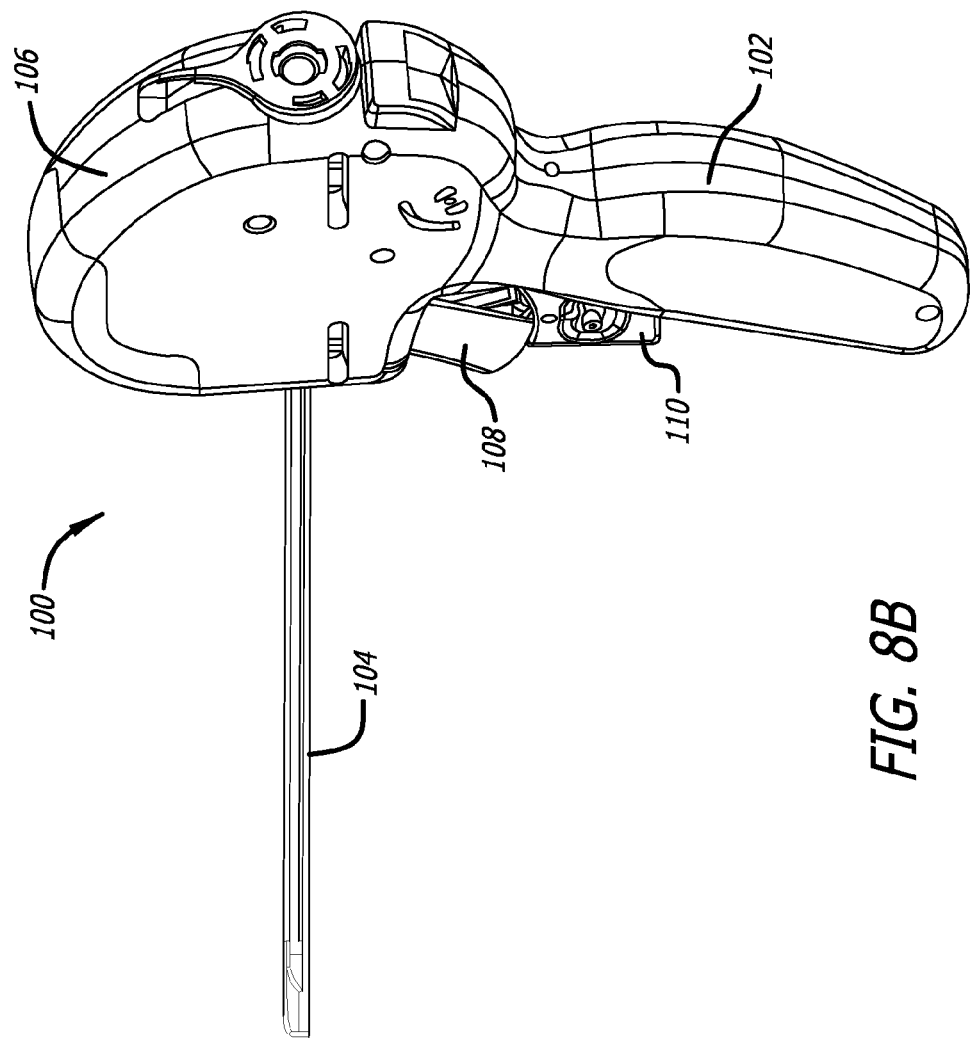

Referring now to FIGS. 8A-C, there is shown one embodiment of a delivery device 100. This device is configured to include structure that is capable of both gaining access to an interventional site as well as implanting one or more implants within a patient's body. The device is further contemplated to be compatible for use with a 19 F sheath. The device additionally includes structure configured to receive a conventional remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to construct an anchor assembly and is sized to fit into a 19 F cystosopic sheath for patient tolerance during a procedure in which the patient is awake rather than under general anesthesia. The tissue access assembly is stiff to allow manual compression of tissue at an interventional site by leveraging or pushing the handle assembly 102.

The anchor delivery device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate delivery of an implant at an interventional site. A needle actuator 108 is provided and as described in detail below, effectuates the advancement of a needle assembly (loaded with an implant) to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needle exits the housing at either the two o'clock or ten o'clock positions relative to a handle grip that is vertical. A needle retraction lever assembly 110 is also provided and when actuated causes the needle assembly to be withdrawn. This action and the structure involved is also described in detail below.

In one particular, non-limiting use in treating a prostate, the elongate tissue access portion 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end thereof reaches a prostate gland (PG). In a specific approach, the side(s) (i.e., lobe(s)) of the prostate to be treated is chosen while the device extends through the bladder and the device is turned accordingly. The distal end of the elongate portion can be used to depress the urethra into the prostate gland by compressing the inner prostate tissue. The inside of the prostate gland (i.e., adenoma) is spongy and compressible and the outer surface (i.e., capsule) of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

As shown in FIGS. 8A-B, the delivery device is at this stage configured in a ready state. The needle actuator 108 and the needle retracting lever 110 are in an inactivated position. Upon depression of the needle actuator 108, the needle assembly 230 is advanced from within the elongate member 104 (See FIG. 8C). The needle assembly can be configured so that it curves back toward the handle as it is ejected. In use in a prostate intervention, the needle assembly is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (i.e. wetness) which may degrade effectiveness of needle penetration.

After complete depression of the needle actuator 108 and the unlocking of the needle retraction lever 110, the needle retraction lever 110 can be actuated. Such action results in a withdrawal of the needle assembly 230. In one embodiment, the needle 230 is withdrawn further than its original position within the device pre-deployment.

Figure 8D:
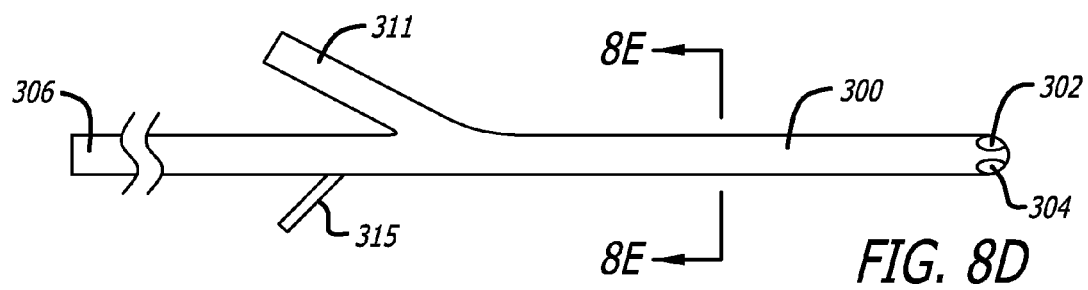
Figure 8E:
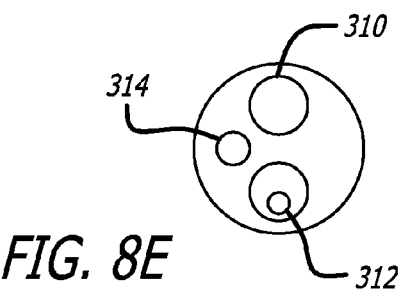
Figure 8F:
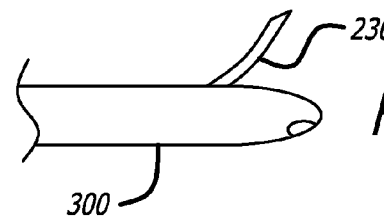

As an alternative, the treatment device can be defined by an elongate catheter 300 (FIGS. 8D-8F). A distal end of the catheter 300 can include two openings, one opening 302 for a working device and a second opening 304 for vision and light. A proximal end 306 of the catheter can be adapted to connect to one or more of a light source and a camera. Extending along a length of the catheter 300 (See FIG. 8E) can be three or more lumens. There can be a first working lumen 310 in communication with the working device opening 302 and a working device channel 311. A second lumen 312 can be sized and shaped to receive camera optics (fibers) and light source fibers connected to the proximal end 306 and can extend to the second distal opening 304. Finally, a third lumen 314 can be provided to extend from an irrigation part 315 to a point near the distal end of the device (not shown). In another embodiment, the working device opening 302 can be moved proximally (See FIG. 8F) so that a working device such as a needle 230 can be extended from a side of the treatment device 300, and perhaps more directly into target tissue.

Figure 9A:
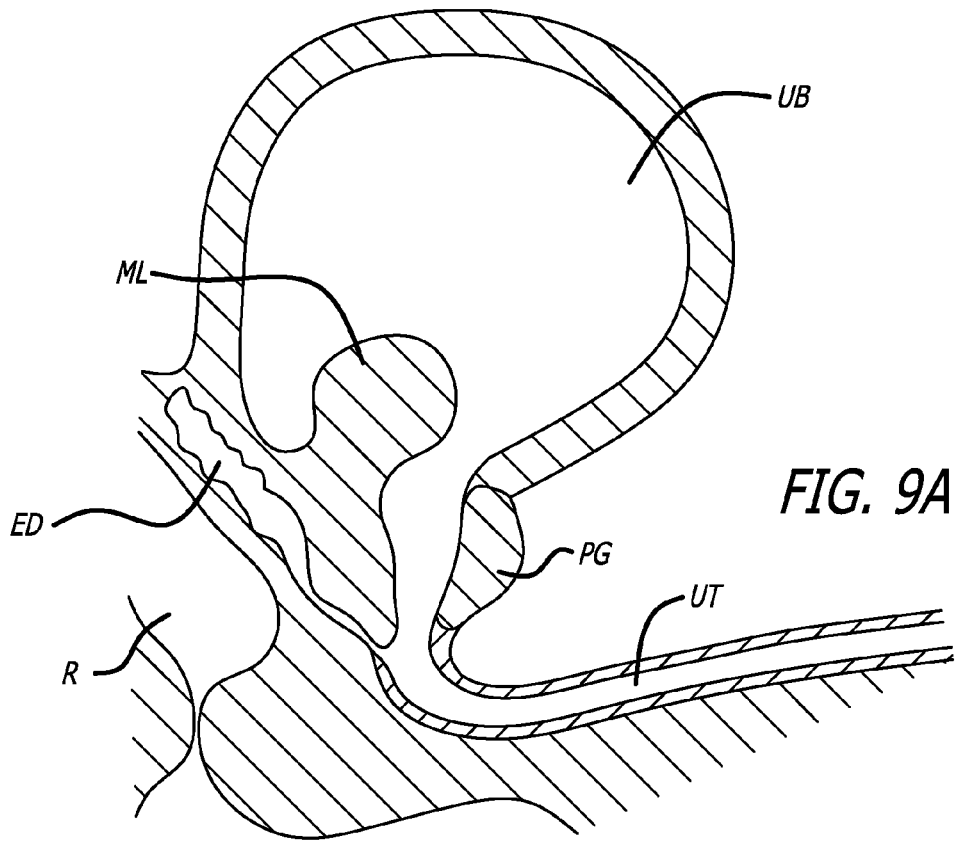
FIGS. 9A-E are various cross-sectional views, depicting details of one approach to treating a median prostate lobe of a prostate.
Figure 9B:
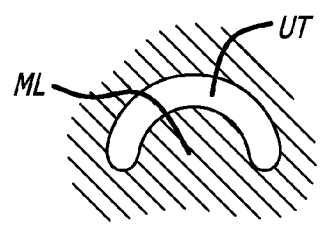

Turning now to FIGS. 9A-B, an approach to treating patients with median lobe ML disease is presented. Such an approach can be used as a complementary therapy with separate treatments for lateral lobes or can be employed to solely treat a median lobe ML. Because an enlarged median lobe ML can extend into the urinary bladder UB and may act as a ball valve interfering with normal function (FIG. 9B is a view through the prostatic urethra and into the urinary bladder), special consideration to moving tissue away from a ball valve location may facilitate accomplishing optimal results. The purpose here being to provide a less invasive means to treat median lobe hypertrophy as compared to TURP and TUIP (transurethral incision of the prostate). By avoiding such invasive approaches, there is minimal risk of disrupting the smooth muscle of the bladder neck and nerve tissue. Additionally, ejaculating function and continence complications will likely be lower. BPH is a very prevalent disease that dramatically affects the quality of life of older men. About 30% of these men have a median lobe that creates a ball-vale effect. The presently disclosed procedure can significantly improve the urinary symptoms of these patients with a much better side effect profile. However, certain previously contemplated procedures currently require patient screening in order to exclude some patients with median lobes requiring treatment because these patients do not respond as readily to the therapy. Because current medical therapy may not be effective on median lobes, these patients only have resection/ablation as available options which both carry significant side effects. The invention treats patients with median lobes without the significant side effect profile due to resection or ablation. The invention preserves the tissue of the prostrate, thus preserving the prostate functions.

Accordingly, an approach involving inserting a band implant into the prostatic urethra UT transurethrally to compress and/or displace the median lobe ML is contemplated. Once the lobe is compressed or displaced, tissue anchors are advanced in a specific direction to maintain the compression/displacement of the median lobe.

Figure 9C:
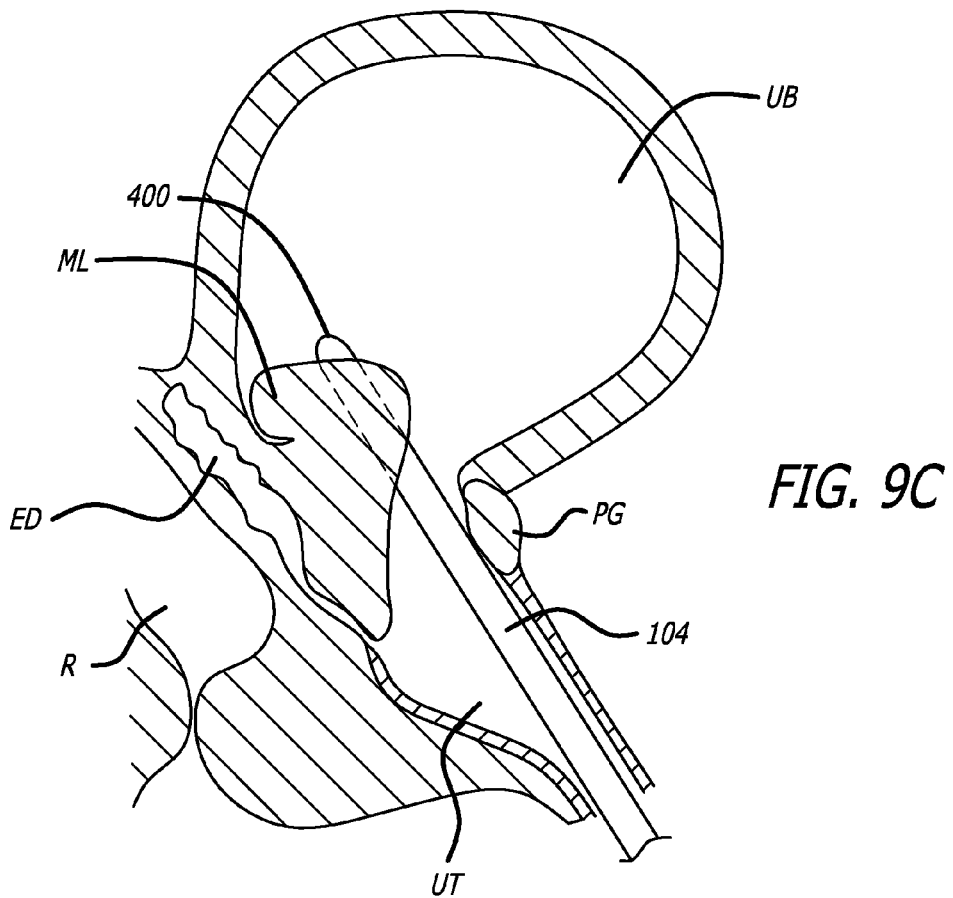

As an initial step, sagittal views of a patient's bladder and prostate can be taken using transabdominal or transrectal ultrasonography. In this way, the patient's anatomy can be assessed. In this regard, an intravesical prostate measurement is taken to determine the vertical distance from a tip of the median lobe protrusion to the base of the bladder. As shown in FIG. 9C, after assessing the anatomy, the elongated tissue access assembly 104 of a device (See FIGS. 8A-B) is advanced within the urethra UT and adjacent the median lobe ML.

Figure 9D:
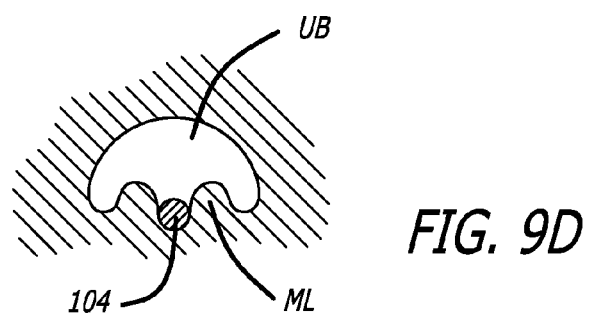

One specific series of actions is to position the delivery device 100, 300 so that its terminal end 400 is in apposition with the median lobe ML (See FIGS. 9C-D).

Next, steps can be taken to cut-off or restrict the nutrient supply to the prostate in order to reduce the size of the prostate. Alternatively, an approach can be taken to remove the median lobe as an obstruction. The arteries supplying the prostate are derived from the internal pudic, vesical and hemorrhoidal. Its veins form a plexus around the sides and base of the gland. Accordingly, an approach to treating the prostate can involve using a minimally invasive method to apply ligature clips or other band implants to tie off or restrict the nutrient supply to the prostate to limit its growth or even to shrink the prostate. This applies to not just the median lobe, but all lobes of the prostate.

In one particular approach, a Foley catheter can be placed into engagement with target tissue. Such a catheter can be implanted by the delivery device and can have a length so that it does not extend outside the body. A suction force can be applied to suck tissue within the catheter and hold in place for a period of time such as 10 days to cause necrosis of the captured tissue. The catheter can further include a coating to help prevent infection or cause necrosis. Once necrosis has occurred the catheter can be removed.

Patients with enlarged median lobe disease might get improved outcomes with a complementary therapy designed specifically for the median lobe. Because the median lobe can extend into the bladder and act as a ball valve, special consideration to moving tissue out of the ball-valve location may be advantageous for optimal results. One purpose is to provide a less invasive means to treat median lobe hypertrophy compared to TURP and TUIP (transurethral incision of the prostate).

Thus, it is contemplated to employ a transurethral delivery device to temporarily constrain a pronounced median lobe and apply a band around the median lobe. The band is left in place for up to 30 days causing tissue necrosis of the median lobe. The median lobe will ultimately sever from the patient and either be voided in the urine stream or be removed via a subsequent intervention. This approach differs from current minimally invasive therapies (TUMT, TUNA), TUIP (transurethral incision of the prostate) and TURP in that is minimally invasive and can treat a median lobe with no cutting or applied energy. Because there is minimal risk of disrupting the smooth muscle of the bladder neck and nerve tissue, ejaculatory function and continence complications will likely be lower than these other therapies. In various additional or alternative steps, self catheterization could be prescribed to address obstruction caused by the severed median lobe until medical intervention can be provided to remove the severed lobe. The delivery device could also use suction or mechanical means to hold and configure the median lobe while applying the restrictive band. The band can be housed within a delivery catheter for transporting and delivering the band at the interventional site. The delivery device can further include a pocket or other recess for accepting prostate tissue about which the band is to be applied. Multiple bands of decreasing size could be applied successively over time to reduce urgency or other symptoms during treatment.

Figure 9E:
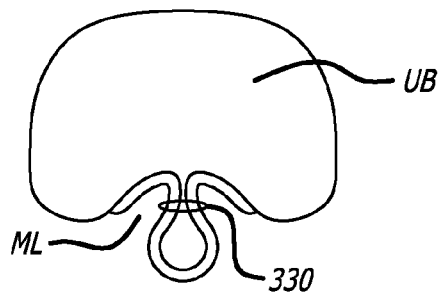

Turning now specifically to FIG. 9E, one specific series of actions is to position the delivery device such that the tip 400 is anterior to a prominent portion of the median lobe ML and then displace the surface in the posterior direction to move the median lobe away from the centerline of the urethral lumen.

The median lobe would then form a tissue fold around the instrument. Once the median lobe ML is compressed or displaced, a tissue wire 330 is advanced in a specific direction to maintain the compression or displacement of the median lobe ML. The wire 330 could then be deployed to hold the median lobe ML in the compressed state. That is, the wire 330 could be in a straight or curved configuration. The wire could be initially straight and take on a curved configuration as it is advanced out of the delivery instrument.

Further, it is contemplated that the wire implant 330 could be metallic or polymeric and could have surface treatments including drugs, elution pores, or tissue ingrowth pores. The cross section of the wire 330 could be round or other shapes (round with ribs, triangular) to enhance mechanical properties, especially bending stiffness. Features such as hinge points or wings also could be added selectively along the length to increase tissue holding forces or adjust bending stiffness of the device.

Figure 10:
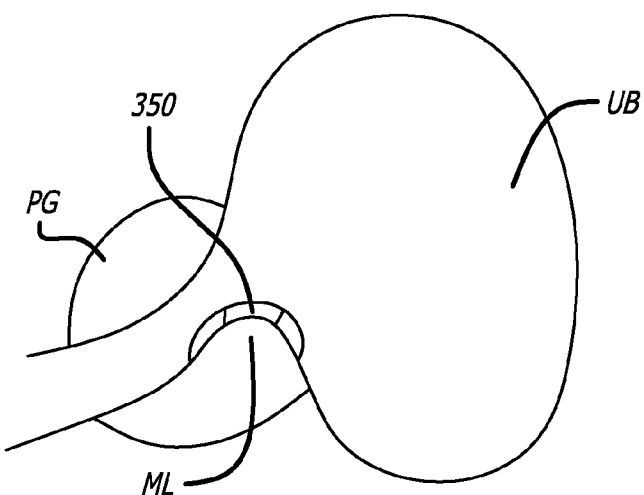
FIG. 10 is a partial cross-sectional view, depicting employing a sling device to compress a median lobe in a first direction.
Figure 11:
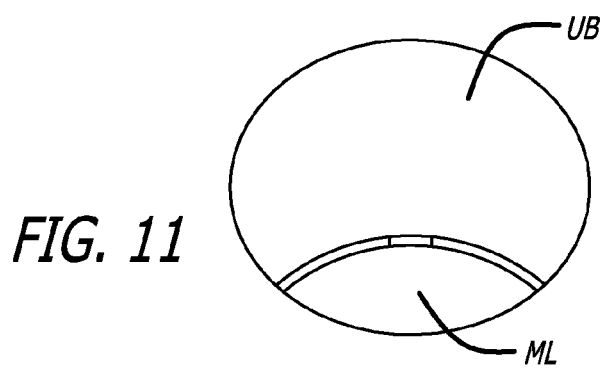
FIG. 11 is a partial cross-sectional view, depicting compressing a median lobe in another direction.
Figure 12A:
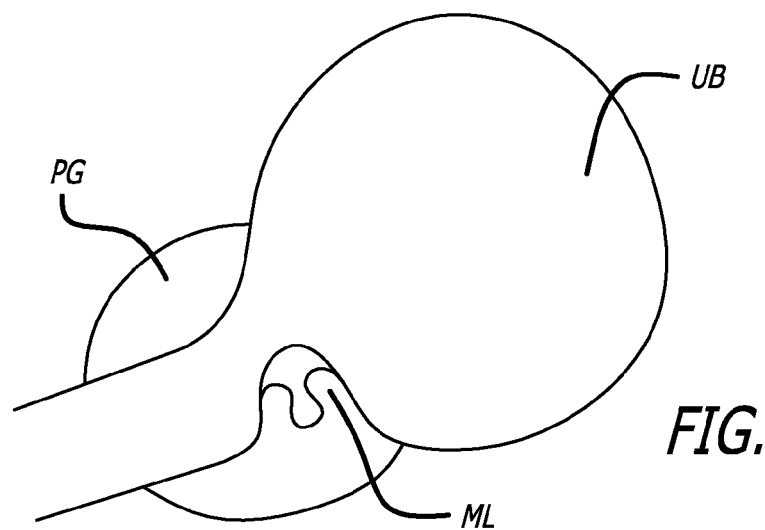
FIGS. 12A-B are partial cross-sectional views, depicting a shaped implant implanted in a median lobe.
Figure 12B:
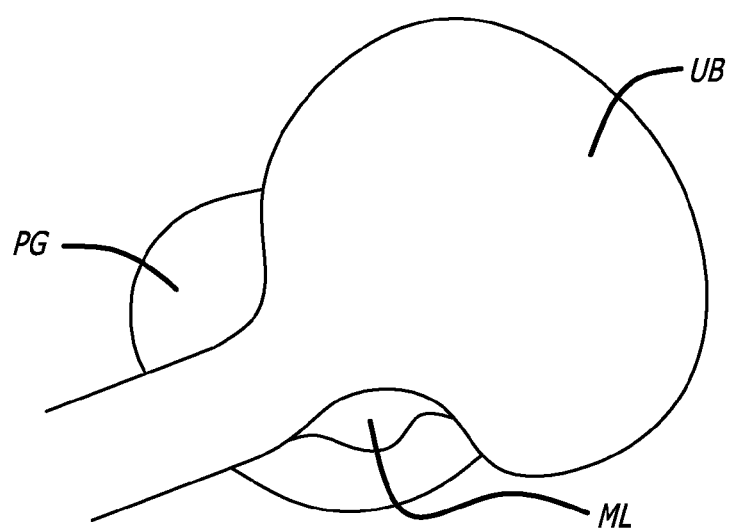

As stated, an enlarged prostate median lobe can lead to lower urinary tract symptoms by obstructing or closing off the bladder neck. It is thus contemplated to address an enlarged median lobe by displacing the enlarged tissue. Accordingly, a sling device 350 can be anchored into the prostate to flatten the enlarged median lobe (See FIG. 10). A transurethral approach could be used to access prostate and deliver the device. As an alternative to the sling design 350 which is anchored proximal to distal, a similar result could be achieved by anchoring the sling 350 in the lateral direction (FIG. 11). Additionally, multiple anchor points could be used to produce a net or web of material which displaces the median lobe. Moreover, a preformed expanding implant 360 (FIGS. 12A-B) can be implanted into the median lobe. In its final shape (FIG. 12B), the implant's net effect would be to flat the median lobe. A transurethral approach would be used to access prostate and deliver the implant.

Figure 13:
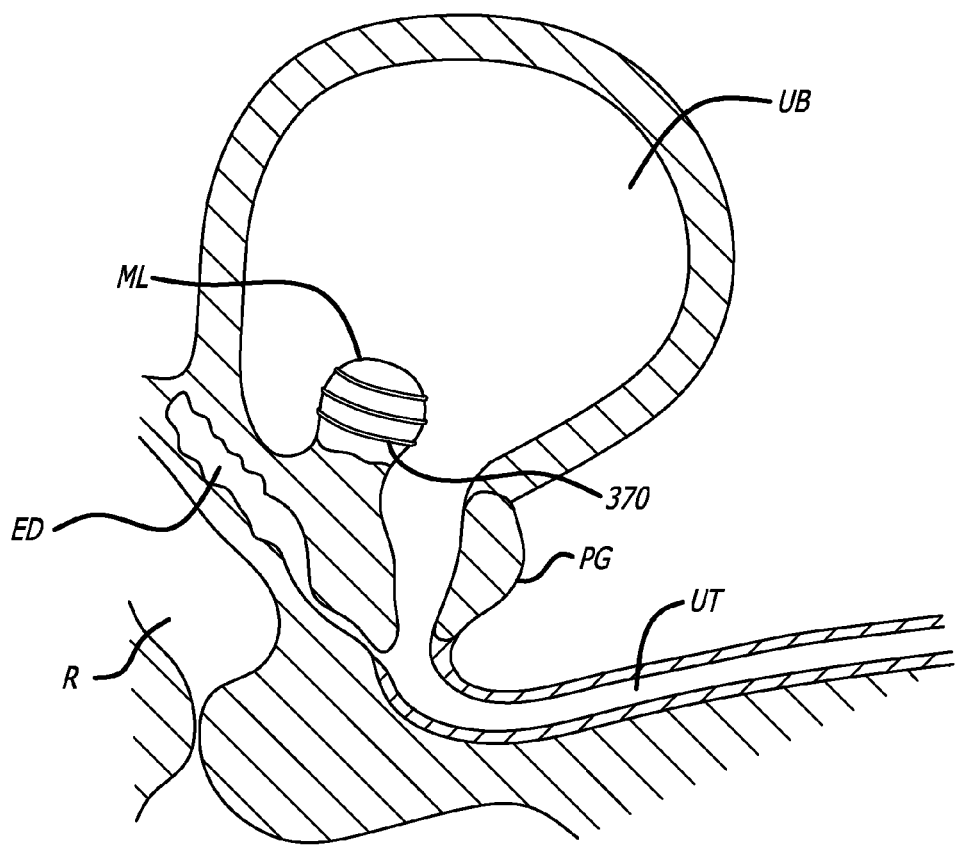
FIG. 13 is a partial cross-sectional view, depicting a band implant wrapped about a median lobe.

In yet another approach, upon accessing the median lobe ML with a delivery device, a Nitinol wire 370 can be fed around the median lobe as shown in FIG. 13. Multiple loops can be formed about the median lobe ML. The act of feeding a pre-formed Nitinol wire 370 compresses and reduces the cross section of the median lobe. It is to be recognized that this approach is not limited to a Nitinol wire, but may include any mechanism that wraps around the median lobe to compress the initial shape.

Figure 14A:
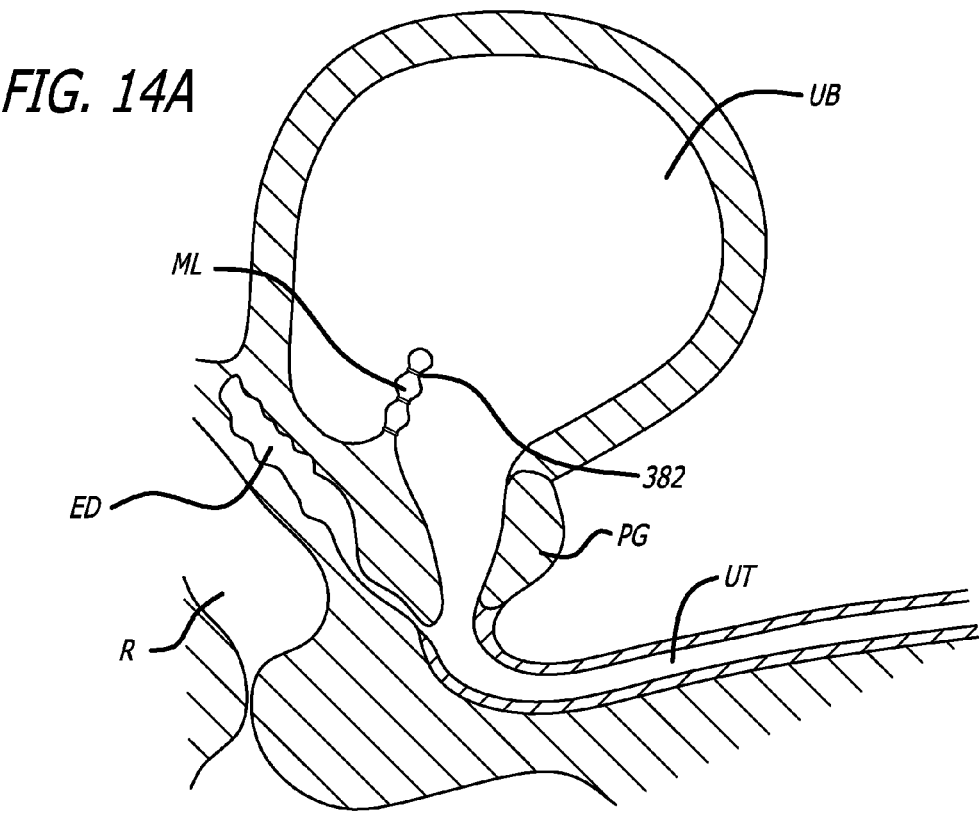
FIGS. 14A-B depict a suture device and the suture device implanted to compress a median lobe.
Figure 14B:
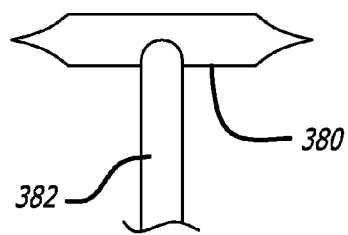

Further, a dual ended needle 380 with a suture 382 can be used to treat an enlarged median lobe ML (See FIGS. 14A-B). Here, the needle 380 is manipulated to penetrate the median lobe ML with the needle 380 going through the median lobe and into the bladder cavity UB. The needle 380 can then be driven back through a new section of the median lobe ML. As the needle 380 with suture is being deployed through the median lobe ML, tension is applied to the suture 382 which compresses the median lobe ML. The act of controlling the needle 380 could be accomplished by an external tool or feature that would redirect the needle 380 upon exit of the median lobe ML. FIG. 14A represents a median lobe ML that has been compressed via deploying a suture through the median lobe ML in multiple locations via the dual ended needle.

Figure 15A:
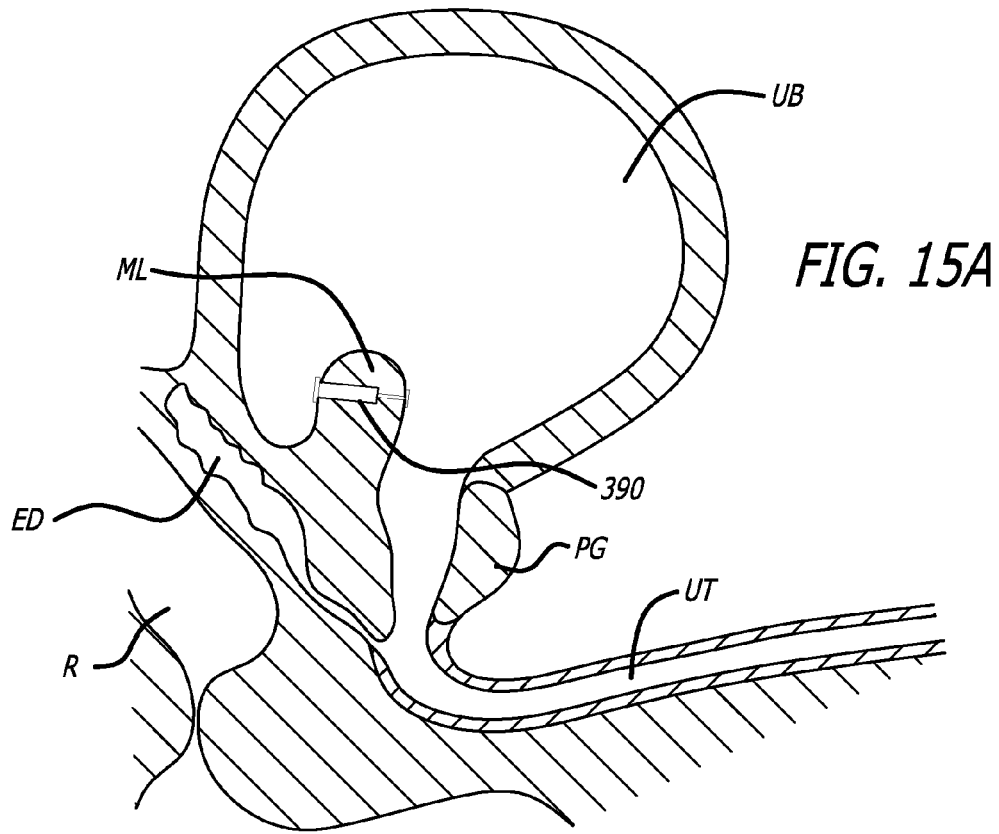
FIGS. 15A-C depict a toggle bolt device and the device implanted to compress a median lobe.
Figure 15B:
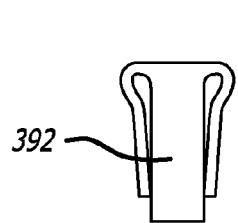
Figure 15C:
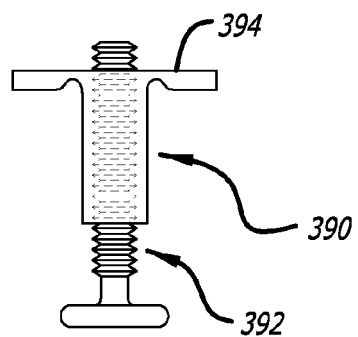

With reference now to FIGS. 15A-C, a restrictive implant in the form of a toggle bolt 390 can be used to compress the median lobe ML in order to reduce its cross section. The toggle mechanism 390 consists of at least two components: a first part 392 has external threads which mate with the internal threads of a second part 394. The second part 394 is initially deployed from one side of the median lobe ML through the other side. The second part 394 has wing features which expand outward once it penetrates through and outside the median lobe ML in the bladder. The wing features may expand based on material properties or a secondary design feature or movement may cause the wings to flare out. Once the wings are expanded outwardly, the second part 394 will be pulled back in order to engage the median lobe ML. This action utilizes rotation of the first part with a tool in order to drive parts toward each other in order to compress the median lobe ML. The first part 392 may also be considered of at least two pieces so that the wings that engage the median lobe ML do not rotate. Thus, the internal bolt mechanism would rotate, but the wing section of the bolt would not be constrained in the axis of the bolt. An alternate approach to driving implant parts together may be achieved through the use of a ratcheting pawl. An advantage of this type of mechanism is that neither implant part would require rotation.

Figure 16A:
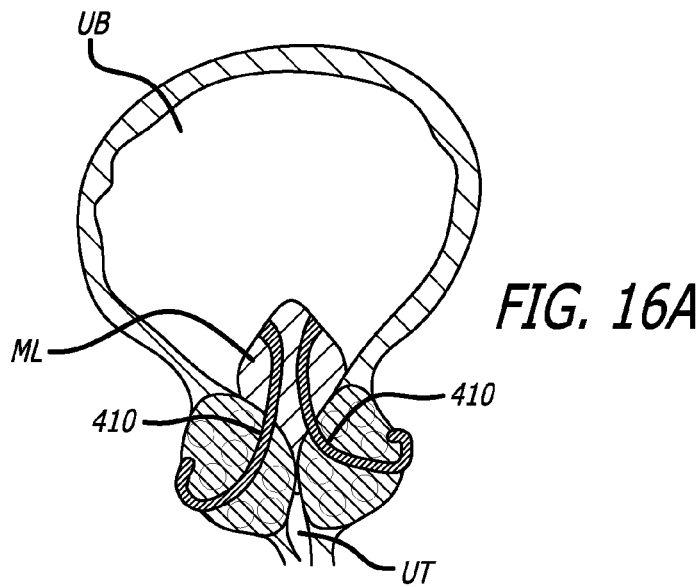
FIGS. 16A-B are partial cross-sectional views, depicting hoop implants compressing a median lobe.
Figure 16B:
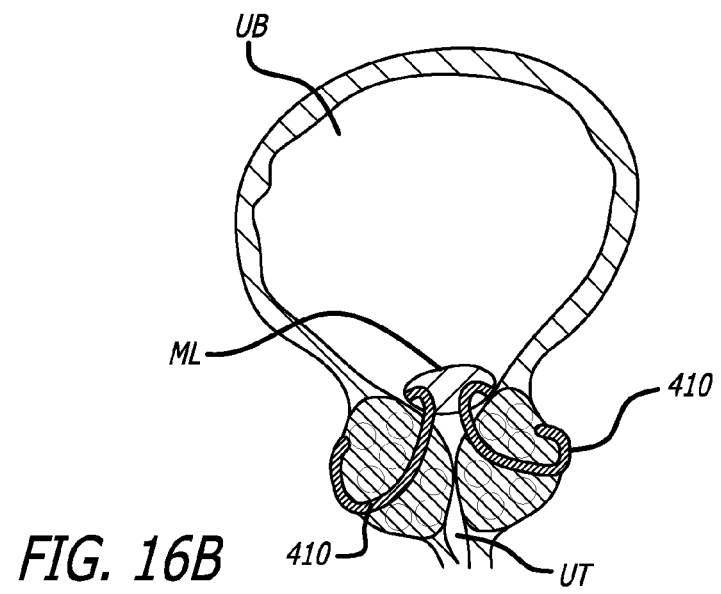

A further median lobe treatment approach (FIGS. 16A-B) can involve a collapsible hoop 410 attached to a flexible extension with a barb or hook at the distal end. The hoop 410 is delivered in its collapsed state transurethrally with a delivery device that attaches the barb or hook of the flexible extension on the implant to the intravasicular portion of the median lobe ML. The hoop 410 pulls the lobe anatomically distal, holding it against the posterior wall of the prostatic urethra UT. In this way, a tissue sparing method of treating an enlarged median lobe ML is provided. It uses a single implant which may be delivered transurethrally. The hoop implant 410 could be a low cost polymer or a simple metal device fabricated from shape-memory material such as Nitinol. The same device could possibly be used to treat enlarged lateral lobes as well as the median lobe. One contemplated alternative to a ring design is multiple single wire implants (not shown) that would be attached by a barb at one end to the intravesicular component of the median lobe ML, and at the other end to the capsule of the prostate by penetrating through the lobe. The wires could be pre-formed and made from shape-memory material or they could be formed in-situ.

Figure 17A:
FIGS. 17A-C depict a collapsible wire implant and the device implanted to compress the median lobe.
Figure 17B:
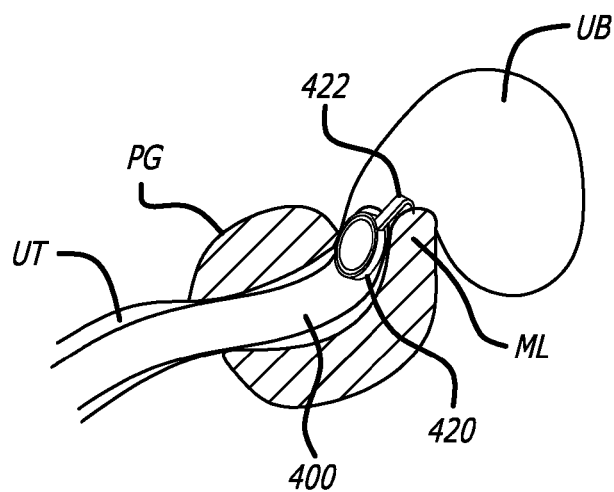
Figure 17C:
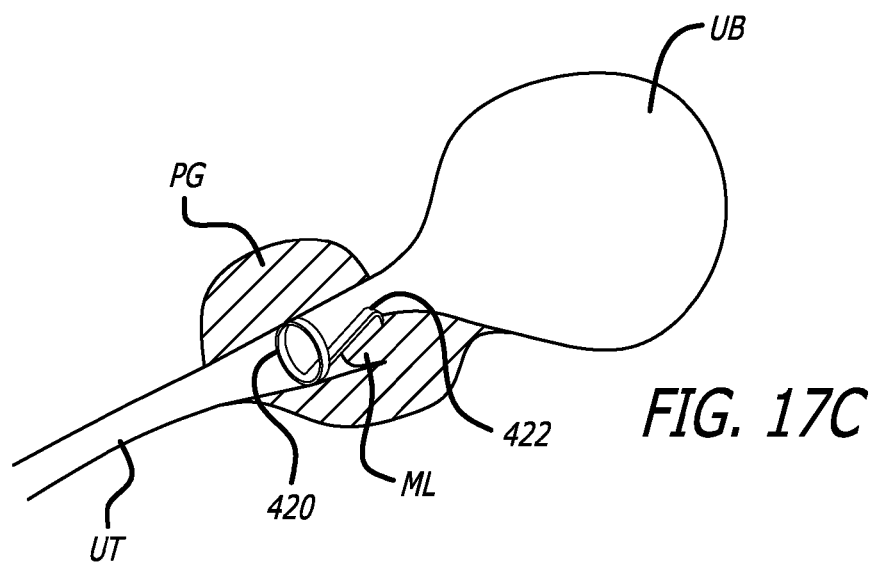

Turning now to FIGS. 17A-C, there is shown a collapsible implant 420 which is configured to attach to the median lobe ML and pull it posteriorly into the prostatic urethra UT. The implant 420 includes a collapsible wire/plastic ring with a hook or barb 422 which is arranged to be inserted into a median lobe ML. In a first step of implant deployment, the implant 420 is held collapsed in a delivery device and advanced within the urethra UT to the median lobe ML. The hook 422 of implant 420 is then inserted into median lobe ML. Next, the implant 420 is configured so that the hook or barb 422 functions to pull the median lobe ML down into the prostatic urethra UT.

Figure 18A:
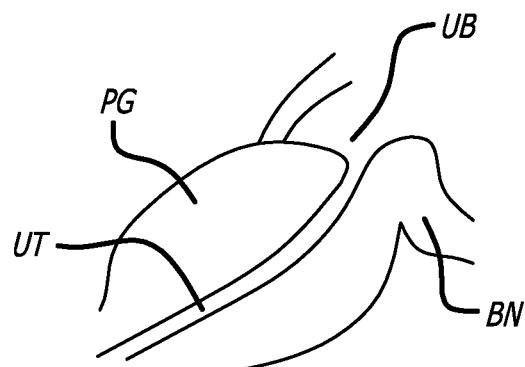
FIGS. 18A-B are partial cross-sectional views depicting employing a band to translate tissue adjacent the prostate.
Figure 18B:
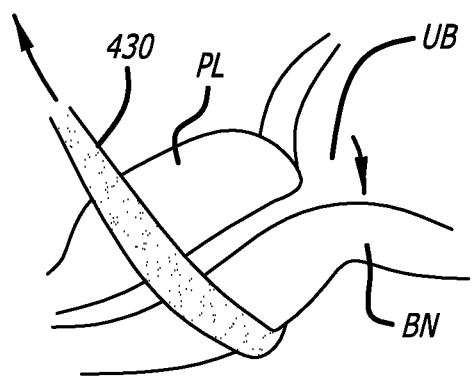

It is to be recognized that the alignment of the prostate with the bladder can exacerbate occlusive effects or tissue hyperplasia. Hypertrophy of the median lobe is more occlusive if the prostate has a high bladder neck BN or sharp angle take off from the bladder floor. Thus, as an alternative approach to treatment (See FIGS. 18A-B), slings or anchors 430 can be used to reposition the prostate PG relative to the bladder UB such that less obstruction exists. Accordingly, the prostate can be lifted anteriorly to reduce occlusion of the median lobe ML. In one approach, the sling 430 could anchor to bone or to peritoneal fascia to thereby alleviate any ball valve action of the median lobe ML.

Such above-described devices can be stand-alones, i.e. not requiring a TRUS probe. The treatment procedures could further accommodate insertion of an ultrasound or other imaging probe into the delivery device for guidance and could have an integrated disposable imaging system. A handle on the needle device can be added to fully or partially automate connector delivery. The handle can have user settings for needle depth. Also, the implants or delivery devices can be coated or doped with antimicrobial materials such as silver. A Foley catheter or other device could also be used to locate the urethra on the TRUS image. In fact, a customized Foley catheter could provide a specific deployment target and a Doppler flow feature on the ultrasound could be sued in conjunction with a Foley catheter to further enhance the target.

Moreover, during a treatment procedure, a second catheter (not shown) with a vision system may be advanced into the urinary bladder UB to allow verification of anchor placement and tensioning of the enlarged median lobe ML from within the urinary bladder UB. The catheter or device may be flexible, rigid or semi-rigid. The needle may exit at the tip of the device, or may exit at the side of the device. Some portion or the entire catheter or device may have articulation control to allow for navigating and positioning.

Accordingly, the present disclosure contemplates treating the body anatomy. In the context of prostate treatment, the present disclosure is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis. Once implanted, the implants of the present disclosure accomplishes desired tissue manipulation, approximation, compression or retraction as well as cooperates with the target anatomy to provide an atraumatic support structure.

Subsequent to the interventional procedure, the patient can be directed to take alpha blockers for 2-4 weeks. Anti-inflammatory medicine can also be taken.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the various disclosed implants or selected portions thereof, can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the implant can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the implants. Such coatings can have various thicknesses or a specific thickness. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is further contemplated that in certain embodiments, the disclosed implants can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

It is to be recognized that various materials are within the scope of the present invention for manufacturing the disclosed devices. Moreover, one or more of the disclosed implants disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the apparatus and approaches have been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A method for treating benign prostatic hypertrophy involving an enlarged median lobe, comprising:
   accessing the median lobe with a delivery device;
   employing the delivery device to deliver an implant about the median lobe; and
   configuring the implant to cause tissue necrosis of the median lobe.

2. The method of claim 1, further comprising removing the necrosed median lobe tissue.

3. The method of claim 1, further comprising configuring a band implant about the median lobe.

4. The method of claim 3, wherein the band implant is housed by the delivery device and the delivery device includes a pocket for receiving tissue about which the band implant is configured.

5. The method of claim 3, wherein the band implant is defined by a wire form.

6. The method of claim 5, wherein the band implant is made from pre-formed Nitinol.

7. The method of claim 1, further comprising wrapping multiple loops of the implant about the median lobe.

8. The method of claim 1, wherein the implant is a dual ended needle with a suture attached thereto.

9. The method of claim 8, further comprising inserting the dual ended needle through the median lobe and into a bladder cavity multiple times to compress the median lobe.

10. The method of claim 1, wherein the implant is embodied in a toggle bolt.

11. The method of claim 10, further comprising configuring the toggle bolt across a section of the median lobe.

12. The method of claim 1, wherein the implant includes a first configuration and a second configuration.

13. The method of claim 12, further comprising delivering the implant to the median lobe in a first configuration.

14. The method of claim 13, further comprising inserting a portion of the implant in contact with the median lobe; and permitting the implant to assume the second configuration.

15. The method of claim 14, further comprising configuring a hook of the implant to engage the median lobe and displace the median lobe when the implant is in the second configuration.

16. The method of claim 1, wherein the delivery device includes a needle and advancing the needle towards the prostate.

17. The method of claim 16, further comprising delivering a second implant into engagement with the median lobe.

18. A method for treating benign prostatic hypertrophy involving an enlarged median lobe at an interventional site, comprising:
    accessing the median lobe with a delivery catheter;
    deploying a Foley catheter so that it engages median lobe tissue;
    applying a suction force so that the Foley catheter captures tissue;
    removing the delivery catheter from the interventional site;
    leaving the Foley catheter in place long enough to allow necrosis of captured tissue; and
    removing the Foley catheter and necrosed tissue.

19. The method of claim 18, wherein the Foley catheter has a length such that it does not extend outside a patient's anatomy when tissue is captured.

20. The method of claim 18, wherein the Foley catheter is coated with a substance to facilitate necrosis.

\* \* \* \* \*